United States Patent [19]

Matsui et al.

[11] Patent Number: 4,809,341

[45] Date of Patent: Feb. 28, 1989

[54] TEST METHOD AND APPARATUS FOR A RETICLE OR MASK PATTERN USED IN SEMICONDUCTOR DEVICE FABRICATION

[75] Inventors: Shougo Matsui, Sagamihara; Kenichi Kobayashi, Tokyo, both of Japan

[73] Assignee: Fujitsu Limited, Kanagawa, Japan

[21] Appl. No.: 72,372

[22] Filed: Jul. 13, 1987

[30] Foreign Application Priority Data

Jul. 18, 1986 [JP] Japan .................. 61-170369

[51] Int. Cl.$^4$ ............................................. G06K 9/00
[52] U.S. Cl. ........................................ 382/8; 358/106; 382/30; 382/47
[58] Field of Search .............. 382/8, 47, 34, 30, 33, 382/42; 358/101, 106, 287, 107; 356/392, 394, 396, 397; 340/731

[56] References Cited

U.S. PATENT DOCUMENTS

| | | | |
|---|---|---|---|
| 4,179,685 | 12/1979 | O'Maley | 382/45 |
| 4,486,775 | 12/1984 | Catlow | 358/106 |
| 4,589,140 | 5/1986 | Bishop et al. | 382/8 |
| 4,603,974 | 8/1986 | Matsui | 356/394 |
| 4,641,353 | 2/1987 | Kobayashi | 382/8 |
| 4,701,961 | 10/1987 | Hongo | 382/34 |
| 4,712,102 | 12/1987 | Troupes et al. | 340/731 |

FOREIGN PATENT DOCUMENTS 2012088A 7/1979 United Kingdom ............... 382/47

*Primary Examiner*—Leo H. Boudreau
*Assistant Examiner*—Joseph Mancuso
*Attorney, Agent, or Firm*—Armstrong, Nikaido, Marmelstein & Kubovcik

[57] ABSTRACT

A test method and apparatus for a reticle/mask pattern used for a semiconductor fabrication is disclosed for a case in which the reticle/mask pattern is modified from the original design data and has a reduced/magnified pattern in a similar shape. The reticle/mask pattern is scanned and detected optically and electrically, and detected signal is converted to video signal and is stored as a real image pattern data in a first video memory. The original pattern data stored in a magnetic tape is read and converted to video signal, and is stored as an original design pattern data in a second video memory. After graphical operation of the original design pattern data in the second video memory, a group of modified pattern data having a gradual change of reduction/magnification ratio can be obtained. One modified pattern data having substantially same reduction/magnification ratio with reticle/mask pattern, is selected. The real image pattern of reticle/mask stored in the first video memory is compared with the above selected modified pattern data, thereby the inspection of the reticle/mask can be performed.

11 Claims, 5 Drawing Sheets

TEST METHOD AND APPARATUS FOR A RETICLE OR MASK PATTERN USED IN SEMICONDUCTOR DEVICE FABRICATION

BACKGROUND OF THE INVENTION

1. Field of the Invention

This invention relates to a test method and an apparatus for a reticle or mask pattern used in fabricating a semiconductor integrated circuit, more particularly to a method in which a real image of a reticle or mask pattern formed by an optical means is compared with a pattern reproduced by a graphical means from an original design data, and thereby the reticle or mask is inspected to determine if it is acceptable or not. More precisely, this invention relates to a test method and an apparatus for the reticle or mask pattern, which is formed with a slight modification by reducing or magnifying the original design pattern in a similar shape.

2. Description of the Prior Art

In fabricating steps of a semiconductor integrated circuit, a plurality of the same patterns are formed on each chip area on a wafer by a photolithography method, and such steps include a formation of an insulating layer, a diffusion or implantation of impurities, a formation of metal layer and the like. In the photolithography technology, the reticle or mask is used to expose a resist layer coated on a wafer corresponding to the pattern to be formed thereon. The reticle has a pattern having a size of 5 to 10 times as large as the real pattern required on the wafer. Its pattern is formed utilizing a pattern generator, wherein the original design data is installed. On the other hand, the mask has a pattern having the same size as the real pattern required on the wafer, and the mask pattern is formed using a reticle.

In an exposure step for the resist layer on the wafer using a reticle, the reticle pattern is directly projected on the wafer with a reduction ratio of 1/5 to 1/10 by a step and repeat process. In using a mask, on the other hand, the mask has plurality of chip patterns same as those required on the wafer, therefore, the mask is placed directly on the wafer and the resist layer is exposed under this mask.

The pattern formed on the reticle is required to be an exact replica of the original pattern of the design data, in other words, a magnified pattern 5 to 10 times as large as the original in a similar shape. However, in forming the reticle pattern, the reticle is subject to an exposure step using a pattern generator, a developing step and the like. On the other hand in fabricating a mask, the mask is subject to exposure steps with a reduction ratio by step and repeat process using the reticle. Therefore, in fabricating process of the reticle or mask, dimensional errors of patterns, growth of flaws, adhesion of dusts and etc. can not be avoided.

Therefore, inspection of patterns formed on a reticle or mask is an important factor. In testing these patterns, a comparison method has been put to practical application, wherein a real image pattern of reticle or mask is formed by optical and electrical means, and is compared with a standard pattern. As the standard pattern, the reproduced pattern from the original design data is used very often recently.

The above comparison method is disclosed in the following U.S. patents.

U.S. Pat. Nos. 4,603,974, Aug. 5, 1986, issued to S. Matsui; 4,641,353, Feb. 3, 1987, issued to K. Kobayashi; 4,673,816, Jun. 16, 1987, issued to S. Matsui and K. Kobayashi; Appl. No. 620,089, Jun. 13, 1984, by S. Matsui and K. Kobayashi.

The design data of the patterns is generally stored in a magnetic tape using a specific format. Generally, the data in the magnetic tape can not be directly used for the pattern generator in reticle fabrication. Furthermore, the above data also can not be used in a test apparatus for reproducing the original pattern which is compared with a real image pattern of reticle or mask. Therefore the design data should be once subjected to a format conversion using a conversion program for the pattern generator or the test apparatus respectively.

In case of forming a pattern on the reticle, for example, a small area of the reticle is sequentially exposed using pattern generator by moving a reticle stepwise, which is loaded on a stage thereof, and the reticle surface is swept in such a way of moving in a X-direction, shifting Y-position intermittently. In this case, the original design data is to be converted into the format conforming with the specifications of the pattern generator.

The pattern generator has a specification of so-called a field which defines an unit area, during which the reticle substrate is exposed while it is stationary. Generally, the pattern generator has an unit field of $100 \times 100$ $\mu m^2$ to $500 \times 500$ $\mu m^2$, and the reticle is exposed one by one at every field until the entire surface of the reticle is exposed.

Similarly, the test apparatus for a reticle or mask pattern has a prescribed unit field and it necessitates a conversion of the original design data matched with the specific format applicable for the test apparatus.

When different processes are expected to be applied for the specific step in fabricating a semiconductor integrated circuit, the test for reticle pattern becomes more intricate. Because the plural reticles, each having a slight modification in pattern dimensions by reducing or magnifying the original pattern with similar shape are often fabricated. Such a slight modification of reticle pattern is achieved only by changing the conditions of an exposure or chemical treatments.

In another case, it becomes necessary to fabricate a reticle having a slight modification of pattern in order to fabricate a semiconductor integrated circuit which has a slightly different characteristic from the original type. In this case, the slight modification of reticle pattern is also performed by changing conditions of an exposure or processes of chemical treatments.

All reticles having a slight modifications as described above are fabricated using the same design data for the pattern generator, however they go through the slight different process such as exposure or chemical treatment and the like. Accordingly, the format conversion of the original design data for the pattern generator is carried out only once, however, plural kinds of reticles each having a slight modification of the pattern are fabricated from the same design data.

However, in testing these reticles, format conversions of the design data corresponding to each pattern modification are necessary in the prior art. It takes a lot of operating hours of a computer and man-hours.

With regard to a very large scale integrated circuit, format conversion of the original design data is carried out by operating a large-scale computer for long hours. Modification of design data and format conversion are necessary for each modified pattern. Other problems concerned with the above conversion are the maintenance of conversion programs and safe keeping of converted pattern data, because many kinds of reticles or masks having a different pattern size are needed and fabricated even for one original type of an integrated circuit. Therefore, a reliable keeping of these data are important.

SUMMARY OF THE INVENTION

As explained in the prior art, the test method of a reticle or mask pattern (hereinafter abbreviated as reticle/mask pattern), which has a slight modification of reduction or magnification, uses a comparison method, in which the real image pattern thereof has been compared with the pattern reproduced from the design data, reproduced pattern being modified for reduction or magnification, its data format being converted to the test apparatus.

An object of the present invention is to make the above modification of design data and related format conversion unnecessary.

Another object of the present invention is to keep up with any slight change of reticle/mask pattern quickly for testing it.

Still another object of the present invention is to increase the reliability in testing a reticle/mask.

The above objects are achieved by providing in a hardware an additional unit of generating a modified pattern data having a slight reduction or magnification of the pattern.

BRIEF DESCRIPTION OF THE DRAWINGS

FIG. 1 is a schematic block diagram of the present invention. A reticle/mask 1 under test (same system is used for both reticle and mask except the magnifying ratio of an optical system), having a pattern modification from the original pattern, is loaded and fixed on stage 3. As stage 3 is moved, reticle/mask 1 is swept by optical system 7 and its pattern image is detected by sensor 5. Detected image signal 4 is transmitted to conversion circuit 6 for conversion into video signal 8 and then the video signal 8 is stored in video memory 9 every time one field is swept.

Figure 1:
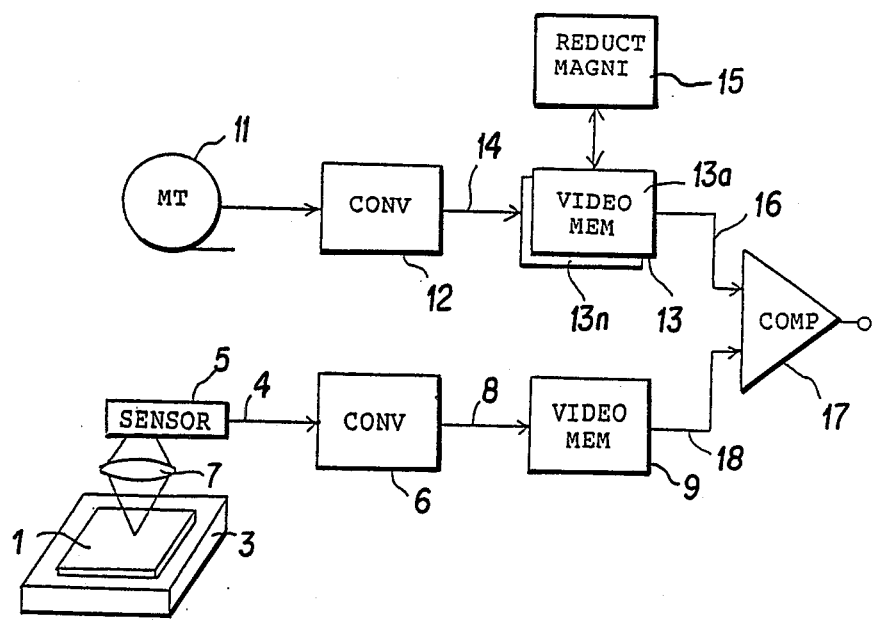
FIG. 1 is a schematic block diagram for explaining the principle of a test method and a test apparatus therefor according to the present invention.

On the other hand, the original design data stored in magnetic tape 11 and converted in advance to the format applicable is used for this test apparatus, however, it is not necessary to be modified for the pattern reduction or magnification. These data are inputted to conversion circuit 12 and the output video signal 14 is then stored in video memory 13 corresponding to above each field of reticle/mask scanning. Video memory 13 provides a plurality of video unit memories 13a to 13n. One of video unit memories 13a, for example, is used for memorizing one field of the original pattern corresponding to the testing field. Video memory 13 is connected to reduction/magnification means 15, which has a function of graphical operation, such as reducing or magnifying the inputted pattern data or slightly shifting the pattern position in the field. The original pattern data stored in video unit memory 13a is subject to graphical operation in reduction/magnification means 15.

Several kinds of modified pattern data each having a gradual change of reduction or magnification ratio are obtained and are stored in respective video unit memories. One of the modified pattern data stored in another video unit memory 13i (not shown), which is theoretical ideal pattern data having almost same shape as actual reticle/mask pattern under test, is selected and is used for test.

Reticle/mask pattern signal 18 outputted from video memory 9 and video signal 16 outputted from video unit memory 13i are inputted to comparison circuit 17, and thus the pattern defects are detected.

DETAILED DESCRIPTION OF THE PREFERRED EMBODIMENTS

Figure 2:
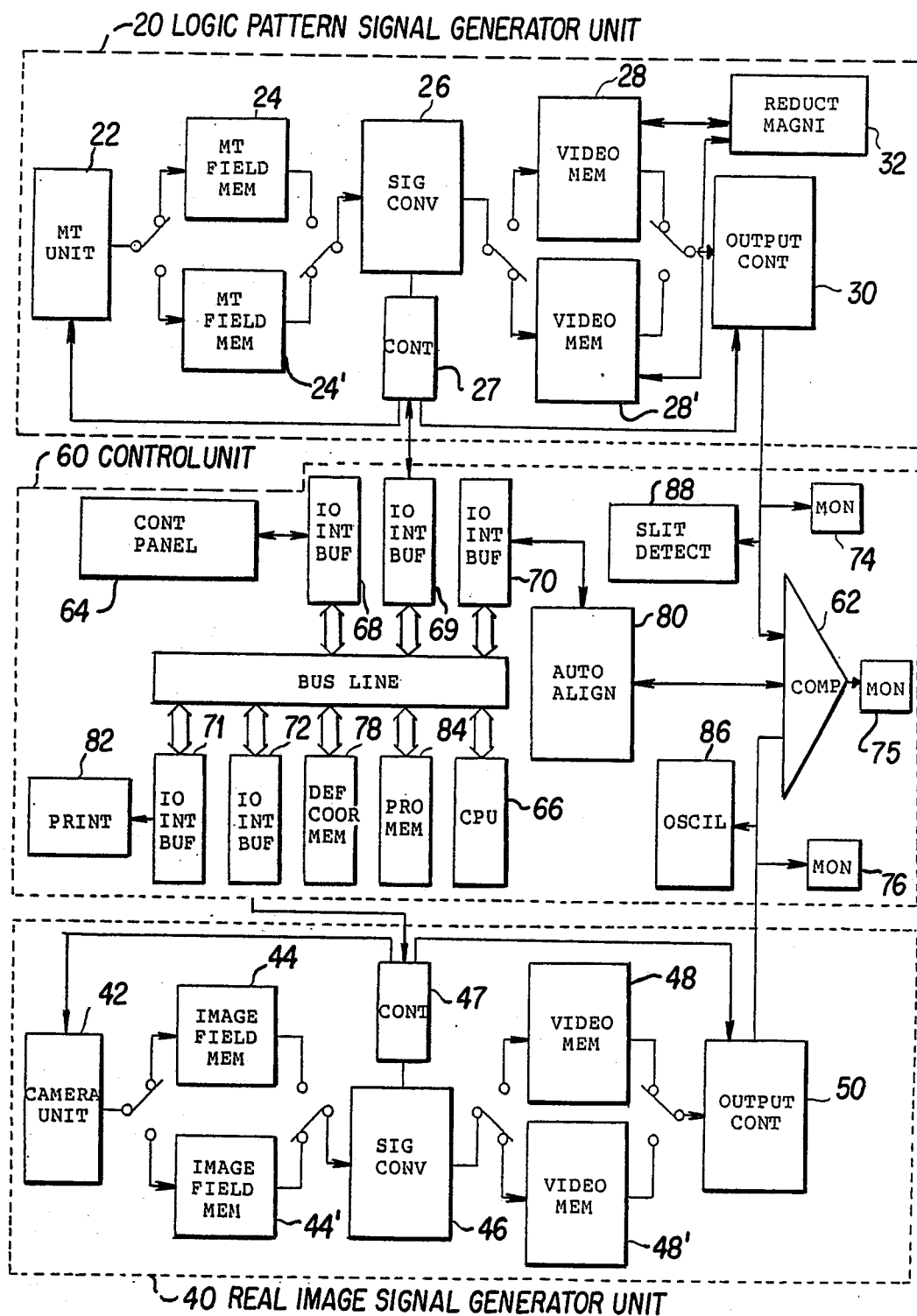
FIG. 2 is a block diagram of an embodiment of the test apparatus according to the present invention.

FIG. 2 shows schematically a block diagram of the test apparatus according to the present invention. Logic pattern signal generator unit 20 comprises magnetic tape (abbreviated as MT hereinafter) unit 22, MT field memory 24, signal conversion circuit 26, controller 27, video memory 28, output controller 30, and reduction/magnification means 32 which constitutes a principal part of the present invention.

Real image pattern signal generator unit 40 comprises camera unit 42 which scans reticle/mask and generates a real image pattern signal, image field memory 44, signal conversion circuit 46, controller 47, video memory 48, and output controller 50.

Control unit 60 comprises comparator circuit 62 which distinguishes between outputs from logic pattern signal generator unit 20 and real image pattern signal generator 40, control panel 64 for whole test apparatus, CPU 66, input/output (abbreviated as IO hereinafter) interface buffers 68 to 72, monitors 74 to 76, memory for defect coordinate 78, automatic alignment circuit 80. Besides the above components, printer 82, program memory 84, oscilloscope 86 for observing waveform, slit detecting circuit 88 and etc. are included. However, these components are not directly related with the present invention, therefore, further explanations for them are omitted hereinafter.

With regard to MT field memory 24, video memory 28, image field memory 44, and video memory 48, each of these four memory components has additional memory 24', 28', 44', and 48' respectively, and each has almost the same structure. These pairs of memories are used by switching from one to another, resulting in a quick data process for the test.

Next, the more detailed structure and function of each component in the test apparatus are explained. Magnetic tape, which records the original pattern data after format conversion, is installed in MT unit 22, and the pattern data is read and extracted therefrom, and is stored stepwise in MT field memory 24 for every one field. When a 1024×1024 bit memory board is used as MT field memory 24 and one bit memory therein is assigned to a small region of 1 $\mu m^2$, then the this memory board represents an area of approximately 1 $mm^2$ of a substrate under test.

The data stored in MT field memory 24 is then inputted to signal conversion circuit 26, where adjustment of the signal level and data correction for the boundary region of the pattern are carried out. And then the signal is inputted to video memory 28 and memorized therein.

Video memory 28 comprises n pieces of unit memories 28a through 28n (not shown), each having, for example, a 1024×1024 bit capacity. Necessary number of unit memories is determined on requirements to adjust an alignment error between the logic pattern and the real image pattern, or necessary reduction/magnification quantity of the original pattern.

The structure and function of reduction/magnification means 32 of the present invention will be explained later. Pattern data having reduction/magnification ratio is stored, for example, in unit memory 28i which is a constituent of video memory 28, and is outputted to comparator circuit 62 through output controller 30.

Figure 3:
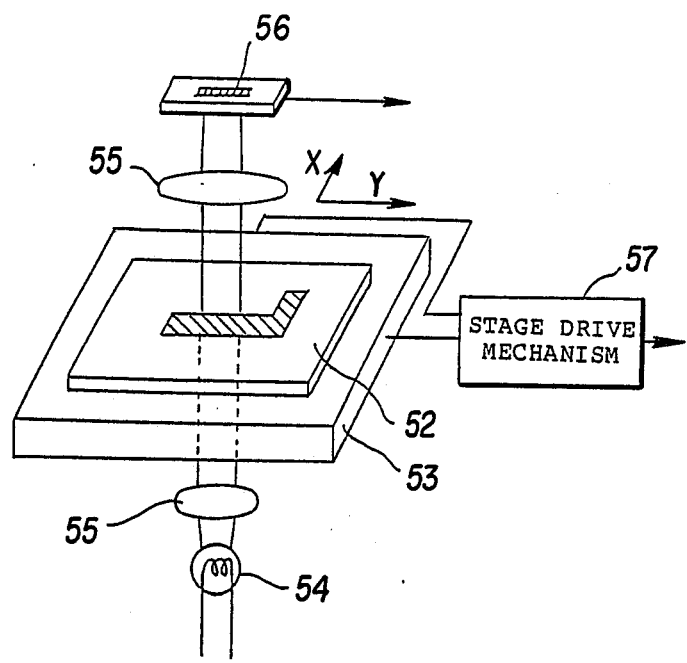
FIG. 3 shows schematically a sensor system for obtaining a real image pattern of reticle/mask under test.

And next, the structure and function of real image pattern generator unit 40 is explained. FIG. 3 shows schematically an example of camera unit 42. Reticle/mask 52 is loaded on stage 53 and is irradiated from back side by light source 54. The light penetrated through reticle/mask is inputted to sensor 56 with an aid of lens system 55. Stage 53 can be moved by stage drive mechanism 57 connected to control unit 60 shown in FIG. 2 of the test apparatus, and the reticle/mask 52 is moved in X-direction and Y-direction. When one dimensional CCD (Charge Coupled Device) having, for example, 1024 detecting elements linearly arrayed is used as a sensor 56 and scans a distance of 1 mm in X-direction detecting the reticle/mask surface of 1 mm length along Y-direction, then an area of 1 mm$^2$ on an object surface is resolved into 1024×1024 bit data and this data is memorized in image field memory 44 of FIG. 2.

In the above described condition, 1 bit of the data represents whether the pattern exists or not in an area of about 1 $\mu$m$^2$. The object area represented by each bit of data varies depending on a magnifying ratio of lens system 55, therefore it is possible to test reticle or mask by changing only the magnification ratio of the lens system.

Signal conversion circuit 46 and video memory 48 in real image pattern signal generator unit 40 in FIG. 2 have almost the same structure and function of signal conversion circuit 26 and video memory 28 in logic pattern signal generator unit 20 in FIG. 2. However, reduction/magnification circuit is not attached to video memory 48, therefore number of unit memories as shown 48a through 48m (not shown) is much smaller than that used for video memory 28.

When the pattern positions have a relative shift or a deviation between two video memories 28 and 48, an alignment procedure becomes important. Therefore, each of video memories 28 and 48 provides a plurality of unit memories. The function of these unit memories is to store each pattern data which is shifted by 1 bit to upper or lower sides, left or right sides, or a combination thereof. Therefore, each video memory provides at least 9 unit memories and is preferable to provide 16 unit memories for further shifts. Automatic alignment circuit 80 in FIG. 2 has a function of selecting the specific unit memories storing substantially the same pattern aligned with each other.

In video memory 28, furthermore, unit memories for storing plural reduced/magnified patterns, each has a gradual difference of reduction/magnification ratio, are required. As a result, the number of unit memories required for video memory 28 becomes much larger.

Two pattern data, one stored in unit memory 48h (not shown) and the other in 28i (not shown), are compared with each other in comparator circuit 62 in control unit 60. If the defect is found, its location is recorded in defect coordinate memory 78.

And next, the details of reduction/magnification means 32 for a pattern are explained. The reduction/magnification of the original pattern data stored in unit memory 28 can be obtained utilizing a computer and a reduction/magnification software installed therein. However, in order to perform the process in a short time, it is better to utilize the following hardware method.

Figure 4A:
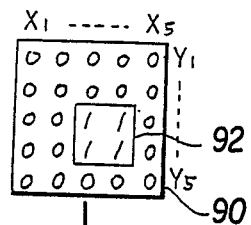
FIG. 4(a) through FIG. 4(e) illustrate memory maps for explaining the principle of graphical operation for reducing or magnifying the pattern data.
Figure 4B:
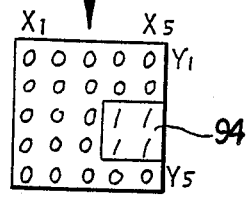
Figure 4C:
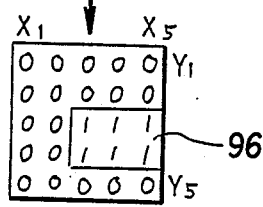
Figure 4D:
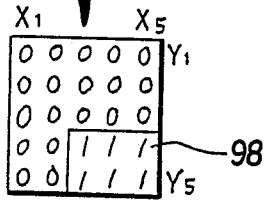
Figure 4E:
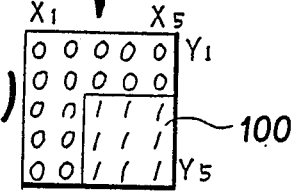
Figure 5:
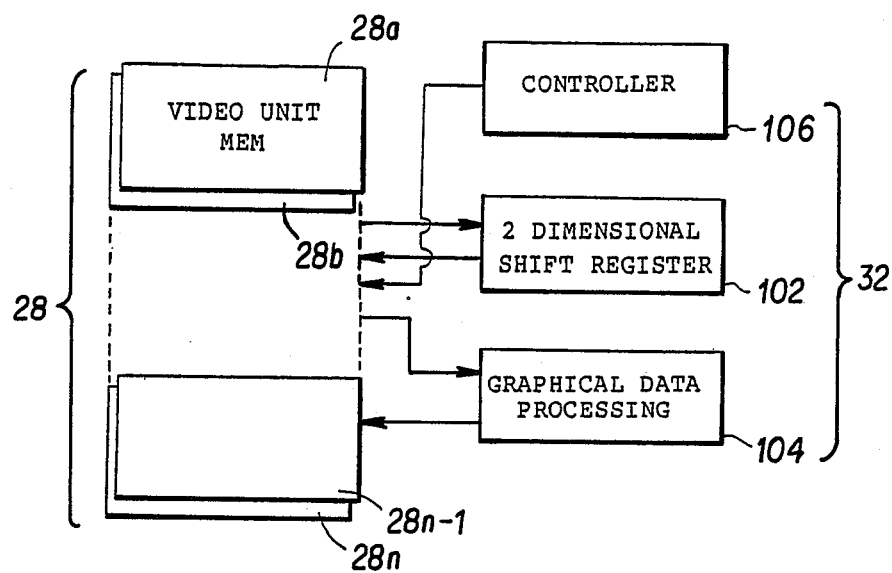
FIG. 5 illustrates a relation between the video memory and the reduction/magnification circuit according to the present invention.

FIGS. 4(a) through 4(e) illustrate the principle applied therefor, and FIG. 5 shows schematically the relation between the video memory 28 and reduction/magnification means 32.

FIG. 4(a) shows a field 90 which is hypothetically defined as consisting of 5×5 bit memories, where the original pattern 92 consisting of 2×2 bit is formed. When the original pattern 92 is shifted to the right side (X-direction) by 1 bit using two dimensional shift register 102 shown in FIG. 5, shifted pattern 94 can be obtained as shown in FIG. 4(b).

And next, graphical operation, in this case OR operation, for pattern 92 in FIG. 4(a) and pattern 94 in FIG. 4(b) is carried out, then it results in forming pattern 96 in FIG. 4(c). This shows original pattern 92 is magnified to the right side (X-direction) by one bit.

Next pattern 96 in FIG. 4(c) is shifted to lower side (Y-direction) by 1 bit, and then pattern 98 in FIG. 4(d) is formed. This shows the original pattern 92 is shifted to the lower side (Y-direction) and magnified to the right side (X-direction) by one bit.

Further, OR operation for pattern 96 in FIG. 4(c) and pattern 98 in FIG. 4(d) produces the pattern 100 in FIG. 4(e) which is shifted and magnified in both X and Y directions.

The above procedure of graphical operation shows just an example. The original pattern data may be shifted by a specified bit number using a shift register and is stored in another unit memory as an intermediate pattern. The graphical operations such as OR, AND, etc. using the intermediate patterns and the original pattern are carried out. And finally the modified pattern data, in other words, reduced/magnified or shifted pattern from the original pattern, can be obtained.

And next, FIG. 5 which shows the relation between the video memory 28 and the reduction/magnification means 32 is explained. The reducing/magnifying or shifting processes of the patterns are carried out by exchanges and operations for data stored in video memory 28 consisting of a plurality of unit memories 28a through 28n using two dimensional shift register 102, graphical data processing circuit 104, and controller 106.

The reduction/magnification of the original pattern can be performed for an entire area or for a limited area of the original pattern. In case of testing reticle/mask pattern having a limited reduction/modification area within the original pattern, this limited area can be easily selected from the control panel 64 shown in FIG. 2. And then the original pattern data for the limited area are subject to reduction/magnification means 32.

And further controller 106 in FIG. 5 has a function of selecting a level of reduction/magnification for either or both X and Y directions. Therefore the present invention may be embodied for a test of reticle/mask having a modified pattern of reduction/magnification only in either X or Y direction only.

In the above embodiment, an area of 1 mm² on object surface is resolved into 1024×1024 bit memory, and 1 bit shift corresponds to 1 μm shift on the object surface. An amount of shift is controlled by controller 106.

The above method has a special feature that the pattern reducing/magnifying processes can be performed in a hardware only without an aid of software, therefore, the results can be obtained very quickly.

Generally, the pattern modification of reticle/mask is performed with a specific reduction/magnification ratio, having a similar shape with the original pattern, in other words, having the same reduction/magnification ratio for both X and Y directions. By selecting the control level of controller 106 in FIG. 5, therefore, the modified pattern which corresponds the real image pattern of reticle/mask having a certain amount of reduction/magnification ratio can be easily selected and obtained from a group of modified patterns stored in video unit memories, each having a gradual change of reduction/magnification ratio.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the forgoing description, and all changes which come within the meaning and range of equivalence of the claims are, therefore, to be embraced therein.

What we claim are as follows:

1. A test method for a reticle/mask pattern wherein data of an original design pattern is provided and utilized for generating the original design pattern, and a pattern formed on the reticle/mask has a dimension which is reduced/magnified from the original design pattern in a subsequent reticle/mask fabrication process at least in one of X and Y directions, said test method comprising the steps of:

scanning and detecting said formed pattern of said reticle/mask, converting the detected signal to a first video signal, and storing said first video signal in a first video memory as a first binary data every time one field is scanned;

reading the data of said original design pattern stored in a recording medium and converting said original design data to a second video signal, and storing said second video signal in a second video memory as an original design binary data every time said field is read;

subjecting said original design binary data to a reduction/magnification means and generating a group of second binary data, each of said group of second binary data having a stepwise charge in reduction/magnification ratio from said original binary data either in one of X and Y directions or in both directions and storing each of said second binary data in said second video memory;

selecting one of said second binary data form said second video memory, which best matches the formed pattern on the reticle/mask; and making a comparison test between said first binary data outputted from first video memory and said selected second binary data from second video memory.

2. A test method for a reticle/mask pattern according to claim 1, wherein said scanning and detecting step further comprises the steps of loading the reticle/mask on a stage, moving said stage in a first direction, and using a detector comprising a plurality of detecting elements linearly arranged in a second direction vertical to the first direction.

3. A test method for a reticle/mask pattern according to claims 1 or 2, wherein said scanning and detecting step further comprises steps of storing said detected signal in a first field memory every time one field is scanned, inputting the output signal from said first field memory to a first signal conversion circuit through which said video signal is obtained.

4. A test method for a reticle/mask pattern according to claim 1, wherein said reading step further comprises steps of storing the original design data in a second field memory, and inputting the data from said second field memory to a second signal conversion circuit through which said second video signal is obtained.

5. A test method for a reticle/mask pattern according to claim 1, wherein said step of generating a group of second binary data further comprises steps of shifting said original design binary data in a coordinate using a shift register and performing a graphical operation using said shifted data.

6. A test method for a reticle/mask pattern according to claim 1, wherein said formed pattern on the reticle/mask is reduced/magnified from said original design pattern in a partial region within an entire area of said reticle/mask.

7. A test apparatus for a reticle/mask, wherein data from an original design pattern is provided and utilized for generating the original design pattern, and a pattern formed on the reticle/mask has a dimension which is reduced/magnified from the original design pattern in a subsequent reticle/mask fabrication process at least in one of X and Y directions, said test apparatus comprising:

a first means for scanning and detecting said formed pattern of said reticle/mask and converting a detected signal to a first video signal and storing said first video signal in a first video memory as a first binary data each time one field is scanned;

a second means for reading the data of said original design pattern stored in recording medium, and converting to a second video signal and storing said second video signal in a second video memory as an original design binary data each time said field is scanned;

a third means for subjecting said original design binary data to a reduction/magnification means, and for generating a group of second binary data, each second binary data having a stepwise change of reduction/magnification ratio from said original design binary data in either one of X and Y directions or in both directions, and storing each of said second binary data in said second video memory; and a fourth means for selecting one of said second binary data which best matches the formed pattern from the reticle/mask, and for making a comparison test between said first binary data in the first video memory and said selected second binary data in the second video memory.

8. A test apparatus for a reticle/mask pattern according to claim 7, wherein each of said first and second video memories comprises a plurality of unit memories, hereby plural pattern data each having a different deviation of pattern position can be stored in said unit memory.

9. A test apparatus for a reticle/mask pattern according to claims 7 or 8, wherein said reduction/magnification means comprises a shift register, graphical data processing circuit and a controller, each operatively connected to said second video memory.

10. A test apparatus for a reticle/mask pattern according to claim 8, wherein said test apparatus further comprises an automatic alignment circuit means for selecting two patterns, one corresponding to said first binary data and the other corresponding to one of said second binary data which best matches the formed pattern of the reticle/mask.

11. A test apparatus for a reticle/mask pattern according to claim 8, wherein said first means for scanning and detecting said formed pattern of said reticle/mask comprises a stage movable in X and Y directions, a light source, a lens system and a sensor having a plurality of detecting elements linearly arranged.

* * * * *